United States Patent [19]

McCrory

[11] Patent Number: 5,346,717
[45] Date of Patent: Sep. 13, 1994

[54] METHOD OF PREPARING DENTAL CERAMICS FOR BONDING

[75] Inventor: Paul V. McCrory, Withington, England

[73] Assignee: The Victoria University of Manchester, Manchester, England

[21] Appl. No.: 961,712

[22] PCT Filed: Jul. 10, 1991

[86] PCT No.: PCT/GB91/01141

§ 371 Date: Jan. 12, 1993

§ 102(e) Date: Jan. 12, 1993

[87] PCT Pub. No.: WO92/00935

PCT Pub. Date: Jan. 23, 1992

[30] Foreign Application Priority Data

Jul. 12, 1990 [GB] United Kingdom ............... 9015364.4

[51] Int. Cl.$^5$ ............................................. A01N 1/02
[52] U.S. Cl. ................................. 427/2.27; 204/192.1; 427/255; 427/527; 427/529; 427/530; 433/218; 433/222.1; 433/223
[58] Field of Search .................... 427/2, 527, 529, 530, 427/255; 204/192.1; 433/218, 222.1, 223

[56] References Cited

U.S. PATENT DOCUMENTS

| | | | |
|---|---|---|---|
| 4,180,911 | 1/1980 | Bullock | 433/9 |
| 4,364,731 | 12/1982 | Norling et al. | 433/218 |
| 4,673,587 | 6/1987 | Kamigaito et al. | 204/192.35 X |
| 4,849,247 | 7/1989 | Scanlon et al. | 204/192.11 X |
| 4,857,131 | 8/1989 | Damico et al. | 156/331.4 |
| 4,902,576 | 2/1990 | Shimura et al. | 428/472 |
| 5,004,646 | 4/1991 | Benham et al. | 428/344 |

FOREIGN PATENT DOCUMENTS 160481 11/1985 European Pat. Off. .
318024 5/1989 European Pat. Off. .

OTHER PUBLICATIONS

Duvigneaud, P. H. et al, "Tin Oxide Coatings on Ceramics," Sprechsaal, vol. 118, No. 5, pp. 402–410, May, 1985.

Vispute, R. D. et al, "Deposition of Tin Oxide Films by Pulsed Laser Evaporation," Chemical Abstracts, vol. 110, No. 8, Feb. 20, 1989, Columbus, Ohio USA, p. 300.

*Primary Examiner*—Michael Lusignan
*Attorney, Agent, or Firm*—Nixon & Vanderhye

[57] ABSTRACT

A method of preparing the fitting surface of a dental ceramic body for subsequent bonding to a tooth with, for example, glass polyalkenoate and resin based cements, including the step of depositing, by a vapour phase deposition technique, directly onto the fitting surface of the ceramic body a strongly adherent coating of an inorganic substance such as tin oxide at a thickness ideally less than 2 microns, the coating being reactive with the cement to provide a durable chemical bond therewith which is not subject to chemical degradation in the oral environment and which will not compromise the aesthetics of the associated dental restoration.

12 Claims, No Drawings

METHOD OF PREPARING DENTAL CERAMICS FOR BONDING

This invention concerns a method of preparing a surface of a dental ceramic body for subsequent fitting to a tooth, by means of improving the bond strength between the fitting surface of the body and certain commercially available dental cements.

Ceramics including high-alumina porcelains and glass ceramics are frequently used in restorative dentistry for the construction of, for example, jacket crowns, inlays or aesthetic veneers. Such materials are particularly useful for these purposes, being chemically inert and bio-compatible in the oral environment, and are aesthetically pleasing.

However, one disadvantage in the use of ceramics is that their inert chemical nature renders them unable chemically to bond directly to certain dental cements such as glass polyalkenoate cements. Consequently, mechanical retention techniques are often used for attachment. Whilst mechanical bonding may be enhanced by etching the fitting surface of the ceramic material to provide a "key" this tends to cause stress concentration locally and potentially weakens the rather brittle material.

One known technique developed to strengthen porcelain jacket crowns, has the additional advantage of overcoming the problem of bonding. It involves the preparation of a "thimble" of platinum foil, coated on both sides with a layer of tin oxide. The ceramic is fired onto the oxide coated outer surface of the thimble whilst the oxide coated inner surface provides a chemically reactive surface for bonding to the cement. Whilst this technique is effective, it involves a multi-stage process and the use of expensive platinum foil, and compromises the aesthetics of the restoration.

Other chemical methods of bonding to dental porcelain exist. The first is a group of chemicals called silane coupling agents, which can be initially effective in bonding to resin-based cements, but are subject to chemical degradation in the oral environment.

An object of the present invention is to provide a method of preparing the fitting surface of a dental ceramic body for subsequent bonding to a tooth using a dental cement, in which the aforementioned disadvantages are avoided. Such a method, according to the present invention, comprises the step of depositing by a vapour phase deposition technique, directly onto said fitting surface of the ceramic body, a strongly adherent coating of an inorganic substance which is capable of reacting with the cement to provide durable bonding to such cement.

Various chemically reactive species are available for this purpose, including, for example, metals and alloys; metal salts; metallic and nonmetallic compounds; glasses, particularly reactive or ion-leachable glasses; and other reactive ceramics. In a specific example, tin oxide is capable of being deposited as a microns-thin layer (ideally less than two microns) directly onto the fitting surface of the dental ceramic.

The selection of a coating material suitable for this purpose is determined such that it shall be bio-compatible, and, with reference to acceptable optical qualities, to be preferably white or off-white or colourless so as not to compromise the aesthetics of the restoration. Since the marginal regions of a ceramic body prepared in accordance with the invention will, in use, be subjected to saliva, acids of bacterial origin and acids originating from both foods and regurgitated gastric contents, it is important to avoid dissolution in the edge regions owing to chemical degradation, which in turn could lead to bond failure. The substance must be insoluble in both cold and hot water and should resist dissolution in low pH environments.

Various methods exist for vapour phase deposition of such materials onto ceramic surfaces, including physical vapour deposition techniques such as evaporation and sputtering, ion implantation and chemical vapour deposition.

Of sputtering techniques perhaps the most appropriate is the ion plating technique which incorporates partial ionisation of the deposition species thus increasing their average energy and enabling better integration of the coating with the substrate. Ion plating (commonly known as "plasma assisted PVD") is a process in which ion bombardment of the substrate may be accomplished by making the substrate a cathode of a low pressure plasma discharge in a mixture of the coating flux and an inert working gas (usually Argon).

The coating may be applied in a two-stage process in which an ion plating technique is used initially to deposit a metal or alloy on the fitting surface of the ceramic body. Such metal/alloy may then be reacted with other elements or compounds or polyanions in order to produce the desired coating. Examples of such post deposition processes include, (i) oxidation in an oxygen containing atmosphere at elevated temperatures, and (ii) additional bonding of the coating, for example by laser processing.

In a direct coating method reactive ion plating may be used to deposit a coating directly onto the ceramic surface.

Two or more such substances may be deposited in a composite structure in order to combine the advantageous features of such substances.

The chemical and physical properties of the coating may be modified after deposition in order to improve still further its adhesion characteristics. For example, the chemical properties, the colour, or the bond strength may be modified by heating a tin oxide layer to reduce or oxidise the coating.

Experimentally, tensile bond strength tests have been carried out on aluminous ceramics pre-coated in accordance with the invention, using a resin based cement. When such tensile testing was carried out on dental porcelain samples, the mode of failure was predominantly cohesive within the porcelain. However, in the case of high alumina-containing ceramics, the primary mode of failure in the well oxidised tin layers was mainly cohesive within the cement.

Examples of such experimental strength tests will now be referred to. In each test the resin-cement used was a phosphate methacrylate cement.

Initially in a controlled experiment common dental porcelain was bonded to a substrate consisting of a nickel chromium rod, and after a period of 7 days the specimen was tested in tension until failure. The strength of the bond between the untreated porcelain and the cement was measured at 3.4 MPa (megapascals). The sample failed due to poor adhesion at the bond interface with the porcelain.

In a second example a dental porcelain sample was pre-coated in accordance with the invention by deposition of tin oxide onto the fitting surface using a reactive ion plating technique with an RF power supply. Failure occurred at 7.8 MPa, and it is believed that failure occurred cohesively within the porcelain. It can be seen that the bond-strength was therefore considerably higher as a result of deposition in accordance with the invention.

In a third example a further controlled experiment was carried out this time with a high alumina-containing ceramic body bonded to a nickel chromium rod. Here, a bond strength of 11.4 MPa was recorded. Adhesive failure between the ceramic and the cement was seen to have occurred.

In a fourth example, a similar high alumina-containing ceramic body was pre-coated in accordance with the invention with a deposit of tin oxide using a reactive ion plating technique with an RF power supply. In this case, a bond strength of 26.7 MPa was recorded, i.e. something like 2½ times greater than the third example in which no deposition was effected.

In a fifth example a similar high alumina-containing ceramic body was pre-coated with a deposition of tin using a direct current sputtering technique and this yielded a bond strength of 12.0 MPa.

In a sixth example the substrate and deposition material were the same as in the previous example except that in this case post-deposition oxidation of the tin coating was carried out thus yielding a bond strength of 17.9 MPa.

In a seventh example a high alumina-containing ceramic body was subjected to deposition of a tin coating, this time by a magnatron sputtering technique and a bond strength of 15.8 MPa was recorded.

In an eighth example in which the ceramic body and coating material were the same as in example seven, post-deposition oxidation of the tin coating was carried out and was found to yield a bond strength of 17.9 MPa.

It will be seen from the above examples that tensile bond strength between a ceramic body and a dental cement is substantially improved by depositing, by a vapour phase deposition technique, directly onto the fitting surface of the ceramic body, a strongly adherent coating of an inorganic substance which is capable of reacting with the cement to provide a durable bond. It is also clear that there are several effective methods of applying the coating and that the technique will be chosen according to the materials selected for the substrate and for the coating. Improvements can be made in certain cases by enhancement of the coating by post-deposition oxidation.

The process of coating the fitting surface of a dental ceramic body may also serve to improve the mechanical integrity of the fitting surface generally.

I claim:

1. A method for preparing the fitting surface of a dental ceramic body for subsequent bonding to a tooth, the method comprising the steps of:

depositing by a vapor phase deposition technique, directly onto said fitting surface of the ceramic body, a strongly adherent coating of a metal oxide; and applying to said metal oxide coating a phosphate methacrylate dental cement which reacts with said metal oxide coating to provide durable bonding of the body to such cement.

2. A method of bonding a dental ceramic body to a tooth, comprising preparing the fitting surface of the body by a method according to claim 1, and fitting the prepared surface to the tooth.

3. A method according to claim 1, wherein said coating is deposited as a layer of less than 2 microns in thickness directly onto said fitting surface of the ceramic body.

4. A method according to claim 1, wherein said metal oxide is selected to be insoluble in water and to resist dissolution in a low pH environment.

5. A method according to claim 1, wherein said coating is effected by physical vapour deposition.

6. A method according to claim 1, wherein said coating is effected by ion plating.

7. A method according to claim 1 wherein said coating is effected by chemical vapour deposition.

8. A method according to claim 1, wherein said coating is effected by ion implantation.

9. A method according to claim 1, wherein said coating is effected by direct current sputtering.

10. A method according to claim 1, wherein said coating is effected by magnetron sputtering.

11. A method according to claim 1, wherein the coating after deposition on the ceramic body is further treated to enhance its colour and its bond strength.

12. A method according to claim 4, wherein said metal oxide is tin oxide.

* * * * *